United States Patent [19]

Baumgarten et al.

[11] Patent Number: 5,091,364
[45] Date of Patent: Feb. 25, 1992

[54] PREPARATION OF IMMUNOLOGICALLY ACTIVE CELL WALL COMPONENTS FROM ARCHAEBACTERIA

[75] Inventors: Jörg Baumgarten; Helmut Brunner, both of Wuppertal; Inge Flesch, Neu-Ulm, all of Fed. Rep. of Germany; Heinz Hildebrand, West Haven, Conn.; Norbert Piel, Erkrath; Michael Sperzel, Wuppertal, both of Fed. Rep. of Germany

[73] Assignee: Bayer Aktiengesellschaft, Leverkusen, Fed. Rep. of Germany

[21] Appl. No.: 559,432

[22] Filed: Jul. 25, 1990

Related U.S. Application Data

[63] Continuation of Ser. No. 168,704, Mar. 16, 1988, abandoned.

[30] Foreign Application Priority Data

Mar. 31, 1987 [DE] Fed. Rep. of Germany ....... 3710606
May 19, 1987 [DE] Fed. Rep. of Germany ....... 3716669

[51] Int. Cl.$^5$ .................... A61K 37/16; A61K 39/02; C07K 3/00; C12N 1/00
[52] U.S. Cl. .......................................... 514/8; 424/92; 530/395; 530/820; 435/243
[58] Field of Search ............... 514/8; 530/350, 395, 530/820; 424/92; 435/243

[56] References Cited

U.S. PATENT DOCUMENTS 4,596,769 6/1986 Shockmon et al. ............. 435/7
5,043,158 8/1991 Sleytr et al. ................... 424/92

FOREIGN PATENT DOCUMENTS 0206942 12/1986 European Pat. Off.
0237401 9/1987 European Pat. Off.

OTHER PUBLICATIONS

Chemical Abstracts, Band 84, Nr. 21, 24. Mai 1976, Seite 197.
Chemical Abstracts, Band 102, Nr. 13, 1 Apr. 1985, Seite 374.
Chemical Abstracts vol. 91, Nov. 1979, Seite 226.
Jones et al., 1987, "Methanes and the Diversity of Archaebacteria", Microbiological Review 151, pp. 135–177, especially pp. 150–151.
Wilkinson et al., Dictionary of Immunology, 3rd Ed., pp. 159–160.
Koch et al., Stiferinge V. Beiträge & Milleilungen, vol. 5/1983, pp. 31–35.
Mescher, M. F. and Strominger, J. L., 1976, "Purification and Characterization of a Prokarystic Glycoprotein from the All Envelope of *Halobacterium Salinarium*", *Journal of Biological Chemistry*, vol. 251, pp. 2005–2014.
Wieland, F. et al., 1980, "Halobacterial Glycoprotein Saccharides Contain Covalently Linked Sulphate", *FEBS Letters*, vol. 120, pp. 110–114.
Kimura, K. et al., 1982, "Immunological Probes for Bacteriorhodopsin", *Journal of biological Chemistry*, vol. 257, pp. 2859–2867.
Yang, L. L. and Haug, A., 1979, "Purification and Partial Characterization of a Procaryotic Glycoprotein from the Plasma Membrane of *Thermoplasma acidophilum*", *Biochimca et Biophysica Acta*, v. 556, pp. 265–277.

(List continued on next page.)

Primary Examiner—Christine Nucker
Assistant Examiner—Hazel Sidberry
Attorney, Agent, or Firm—Sprung Horn Kramer & Woods

[57] ABSTRACT

A process for the preparation of glycoproteins and proteins from cultures of archaebacteria, comprising culturing archaebacteria, isolating glycoprotein and/or protein from the archaebacteria or their cell walls, enzymatically degrading the glycoprotein and/or protein, purifying and isolating the degradation products, and separating those fractions in the individual purification steps based on the biological activity of the fraction. The products increase the body's defenses against infection.

7 Claims, 3 Drawing Sheets

OTHER PUBLICATIONS

Jones, W. J. et al., 1987, "Methanogens and the Diversity of Archaebacteria", *Microbiological Reviews*, v. 51, pp. 135–177.

Lehninger, A. 1975, *Biochemistry*, pp. 66–67, Worth Publishers, Inc., New York, N.Y.

Bach, J. F. 1982, "Immunomanipulation", in *Immunology*, 2nd Ed., ed. Bach, J. F., John Wiley & Sons, New York, pp. 942–965.

Fauve, R. M., 1982, "Nonspecific Immunity", in *Immunology*, 2nd ed., ed. Bach, J. F., John Wiley & Sons, New York, pp. 449–464.

Biological Abstracts, Band 80, 1985.

PREPARATION OF IMMUNOLOGICALLY ACTIVE CELL WALL COMPONENTS FROM ARCHAEBACTERIA

This application is a continuation of application Ser. No. 168,704, filed Mar. 16, 1988, now abandoned.

The invention relates to a process for the preparation of cell wall components from archaebacteria, to medicaments containing such cell wall components, and to the use thereof for defense against infections.

It has been found that proteins, glycoproteins and glycopeptides which can be obtained from certain groups of archaebacteria can be used for defense against infections, in particular as immunologically active products Archaebacteria are described in detail in The Bacteria, A Treatise on Structure and Function, Vol. VIII, Archaebacteria, Academic Press Inc., 1985; Archaebacteria, edited by Otto Kandler, Gustav Fischer Verlag, Stuttgart, New York 1982 and Archaebacteria, J. Mol. Evol. 11, 245-52 (1978), C. R. Woese et al.

The chemistry of the cell envelopes of the archaebacteria was one of the first phenotypical characteristics used to distinguish the archaebacteria from the normal eubacteria. The murein which is a normal cell envelope component of the eubacteria is not found in archaebacteria. On the other hand, there are cell wall polymers such as pseudomurein, heteropolysaccharides or glycoproteins. The cell envelope of most of the *Gramnegative archaebacteria* is formed by only a surface layer (S layer) composed of regularly arranged glycoproteins.

These S layers are found in thermoacidophiles, in halobacteria and in Gram-negative methanogens. In addition, the sheaths in which certain methanogenic archaebacteria are enclosed consist of glycoproteins (The Bacteria, Vol. 8, Chapter 9: "The Envelopes of Archaebacteria", Otto Kandler, Helmut König.)

The invention relates to a process for the preparation of glycoproteins and proteins from cultures of archaebacteria, which is characterized in that archaebacteria are cultured, and the glycoprotein or protein of the archaebacteria is isolated.

The invention also relates to a process for the preparation of glycoproteins and proteins from cell wall components of archaebacteria, which is characterized in that archaebacteria are cultured, and the cell wall protein of the archaebacteria is isolated.

The invention further relates to a process for the preparation of glycoproteins and proteins from archaebacteria, which is characterized in that archaebacteria are cultured, the glycoprotein and/or protein of the archaebacteria is isolated, the glycoprotein and/or protein is enzymatically degraded, and the degradation products are purified and isolated, with the selection of the fractions in the individual purification steps being based exclusively on the biological activity of the fraction.

Finally, the invention relates to a process for the preparation of cell wall components from cell cultures of archaebacteria, which is characterized in that archaebacteria are cultured, the cell wall components of the archaebacteria are isolated, the cell wall components are enzymatically degraded, and the degradation products are purified and isolated, with the selection of the fractions in the individual purification steps being based exclusively on the biological activity of the fractions.

The invention likewise relates to the products prepared by the said processes.

Suitable for the purposes of the invention are archaebacteria of the orders Halobacteriales, Methanobacteriales, Methanococcales, Methanomicrobiales, Thermoplasmales, Sulfolobales and Thermoproteales. Preferred families within the scope of these orders are Halobacteriaceae, Methanobacteriaceae, Methanothermaceae, Methanococcaceae, Methanomicrobiaceae, Methanoplanaceae, Methanosarcinaceae, Thermoplasmaceae, Sulfolobaceae, Thermodiscaceae, Pyrodictiaceae, Thermoproteaceae, Desulfurociocccaceae and Thermococcaceae. The preferred genera in hese faimilies are those of Halobacterium, Halococcus, Methanobacterium, Methanobrevibacter, Methanothermus, Methanococcus, Methanomicrobium, Methanogenium, Methanospirillum, Methanoplanus, Methanosarcina, Methanothrix, Methanolobus, Thermoplasma, Sulfolobus, Thermodiscus, Pyrodictium, Thermoproteus, Thermofilum, Desulfyrococcus, Thermococcus and the species *H. halobium, Hc. morrhuae, M. formicium, M. byrantii, M. thermoautotrophicum, Mb. ruminantium, Mb. arboriphilua, Mb. smithii, Mt. fervidus, Mc. vannielii, Mc. voltae, Mc. thermolithotrophicus, Mm. mobile, Mg. cariaci, Mg. marisnigri, Msp. hungatei, Mp. limicola, Ms. barkeri, Mtr. soehngenii, Ml. tindarius, Th. acidophilum, S. acidocaldarius, S. solfataricus, Td. maritimus, P. occultum, P. brockii, Tp. tenax, Tp. neutrophilua, Tf. pendens, Tf. spec., D. mobilis, D. mucosus, D. saccharovorans, Tc. celer, Tc. spec.*

Archaebacteria which have glycoproteins as cell envelopes are, in particular:

---

1. Thermoacidophilic archaebacteria
   for example  *Desulfococcus multivorans* (DSM 2059)
   *Sulfolobus acidocaldarius* (DSM 639)
   *Sulfolobus solfataricus* (DSM 1617)
2. Halobacteria
   for example  *Halobacterium salinarium* (DSM 668)
   *Halobacterium halobium* (DSM 670)
   *Halobacterium saccharovorum* (DSM 1137)
   *Halobacterium* sp. (DSM 1411)
3. Gram-negative methanogens
   for example  *Methanoplanus limicolus* (DSM 2279)
   *Methanomicrobium mobile* (DSM 1539)
   *Methanolobus tindarius* (DSM 2278)
   *Methanogenium thermophilicum* (DSM 2373)
   *Methanogenium marisnigri* (DSM 1498)
   *Methanogenium cariaci* (DSM 1497)
   *Methanococcus voltae* (DSM 1537)
   *Methanococcus mazei* (DSM 2067)
   *Methanococcus vannielii* (DSM 1224)

---

The starting bacterium which is preferably used for the cell cultures for the process according to the invention is *Halobacterium salinarium* (DSM 668) or *Halobacterium halobium* (DSM 671).

The invention further relates to medicaments containing cell wall components from cultures or cell walls of archaebacteria, in particular medicaments for defense a9ainst infections, which contain such cell wall components from cultures or cell walls of archaebacteria.

The invention likewise relates to the use of cell wall components from cultures or from cell walls of archaebacteria for the preparation of medicaments especially suitable for stimulating defense against infections.

The cell wall components are proteins, glycoproteins and/or glycopeptides.

The process according to the invention is carried out as follows, for example:

To isolate the cell wall components having an immunostimulating action, the archaebacteria are cultured in a conventional nutrient solution as described in the DSM Catalogue of Strains The glycoproteins are isolated from the cell envelopes by phenol extraction following delipidation of the cells using a chloroform/methanol mixture Alternatively, the cell envelopes can be solubilized by ionic and non-ionic detergents, for example SDS. Furthermore, the cell wall proteins can be enzymatically degraded directly, without previous solubilization. The solubilized cell envelopes are then subjected to an enzymatic cleavage The enzymatic degradation of glycoproteins from cell walls of archaebacteria can be carried out by trypsin, subtilisin, pronase, chymotrypsin, pepsin, proteinase K, papain, carboxypeptidase A, B, P or Y, elastase, pepsin and thermolysin, as well as by combination of the various enzymes.

The enzymatic cleavage products and/or native glycoproteins are worked up by separation on the basis of molecular weight, by ion exchange chromatography and/or by hydrophobic chromatography.

Both the glycoproteins from the cell envelopes of the archaebacteria and the fractions (glycopeptides) resulting from the purification after the enzymatic cleavages have immunostimulating properties.

The invention will be further described hereinbelow with reference to the accompanying drawings wherein.

Figure 1:
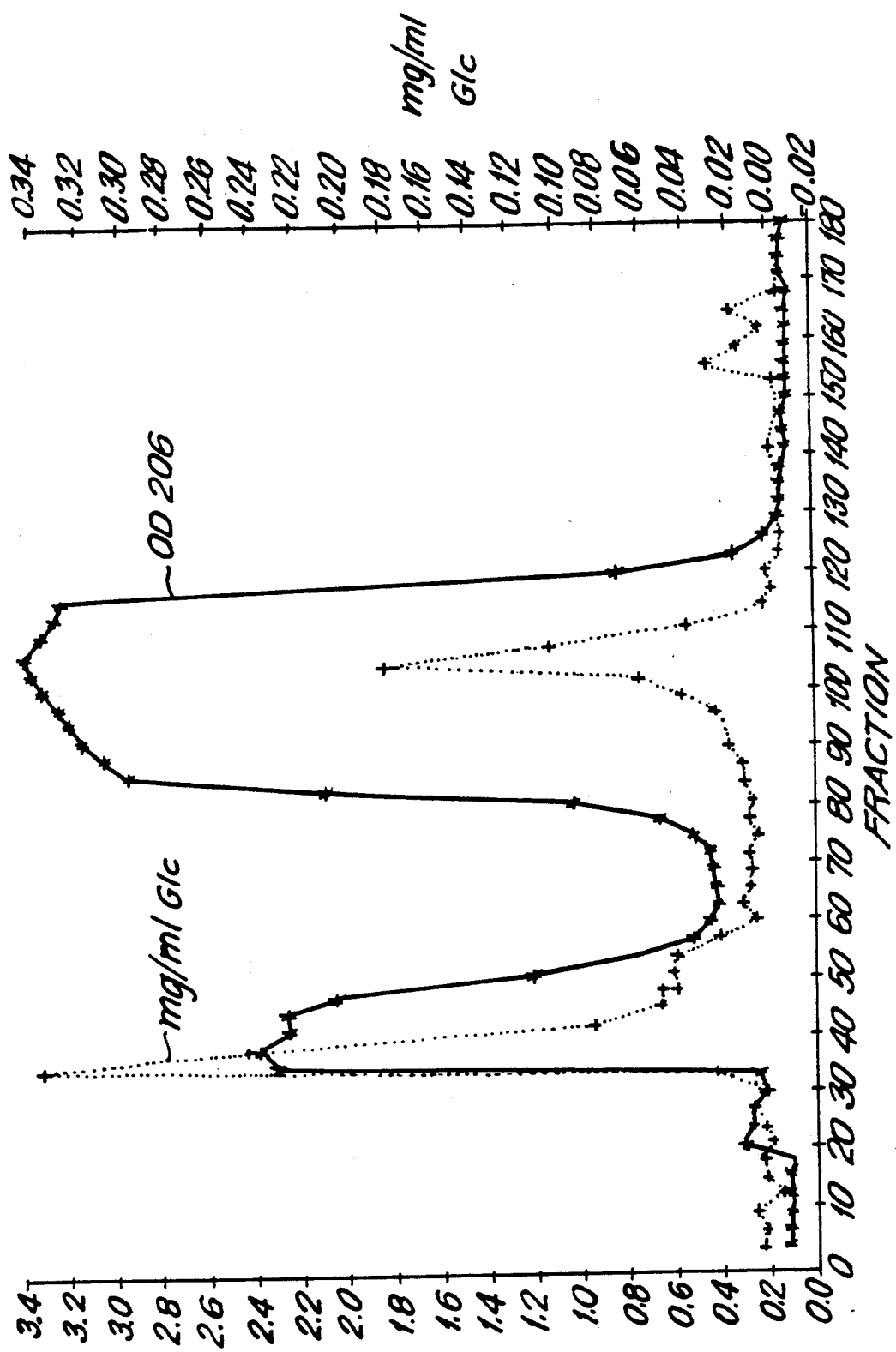
FIG. 1 is an elution diagram of a chromatographed degradation product in accordance with the invention.

Examples of the isolation of immunostimulating substances

Example 1

Culturing of *Halobacterium salinarium* (DSM 668) and *Halobacterium halobium* (DSM 671)

The nutrient solution for culturing Halobacterium had the following composition:

7.5 g of casamino acids; 10 g of yeast extract; 3.0 g of Na citrate; 2 g of KCl; 20 g of $MgSO_4.7 H_2O$; 0.05 g of $FeSO_4.7 H_2O$; 0.2 mg of $MnSO_4.H_2O$; 220 g of sea-salt; of $H_2O$.

A bubble column containing 90 liters of nutrient solution was inoculated with 10 liters of a 4-day old preculture of halobacterium, and incubation was carried out at 37° C. for 8 days aerating with 2.5 m3/h air. The cultured cells were harvested in a Cepa rod centrifuge (duration of centrifugation 2 h). A culture of *Halobacterium salinarium* produced 1,470 g wet weight of cells. A culture of *Halobacterium halobium* produced 2,215 g wet mass of cells.

Example 2

Isolation of the cell wall glycoprotein from *Halobacterium salinarium*

90 l of culture broth were clarified in a continuous flow centrifuge (Cepa rod centrifuge type); the clear material flowing through was discarded. The cells (1,470 g wet mass) were suspended in 3 l of water and disrupted by passing once through a Dyno-Mill (flow rate 0.8 l/h; size of the glass beads about 0.1 mm). For delipidation, this was stirred into 60 l of a mixture of dichloromethane and methanol (2 l), which was then stirred for 3 h and left to settle overnight The still slightly reddish sediment was washed with 5 to 10 l of the same mixture (until it had a bright white color) and dried in a vacuum drying oven at room temperature. Yield 743.6 g.

For further enrichment of the cell wall components, this fraction was subjected to phenol extraction by suspending it in 5.0 l of 0.05 M tris-HCl buffer, pH 7.2, with the addition of 3,960 g of phenol and 45 g of KCl.

After mixing in a cold room for 2.5 h, the mixture was clarified by centrifugation (2,000 rpm, 50 min) and the upper phase was dialyzed against distilled water (for about 3 days, until the odor of phenol was no longer perceptible). Insoluble constituents were removed by centrifugation, and the clear supernatant was freeze-dried.

Yield: 2.21 g.

Example 3

Isolation of glycopeptides from glycoprotein

A. Trypsin degradation of the glycoprotein fraction 2.21 g of the cell wall component fraction were dissolved in a solution, which had been sterilized by filtration, of 210 mg of trypsin and 240 mg of sodium azide in 0.05 M tris-HCl buffer, pH 7.2, and were incubated at 37° C. for 24 h. The mixture was then chromatographed in portions (8 portions) on Ultrogel AcA 44 (flow 40 ml/h; eluant water), the eluate being examined for carbohydrate-containing fractions using the anthrone test. These fractions were combined and freeze-dried (see FIG. 1; elution diagram of an Ultrogel column chromatography).

Yield: fraction I 228.6 mg; fraction II 1526.7 mg. Fraction II had immunostimulating activity.

B. Subtilisin degradation of the carbohydrate-containing fraction 1526.7 mg of fraction II from the Ultrogel separation were dissolved in a solution, which had been sterilized by filtration, of 27 mg of sodium azide and 153 mg of subtilisin in 134 ml of tris-HCl buffer (0.05 M, pH 8.0) and were incubated at 37° C. for 24 h. The solution was then either worked up further immediately (see section C) or stored at −20° C.

C. Purification on CM-Sephadex and Biogel P-2

CM-Sephadex was converted into the Na+form using NaCl (2 M solution), and the pH was adjusted to 7.0 with Na phosphate (5 mmol/l). The solution from B (see above), which had been clarified by filtration, was pumped through the column at 16.7 ml/min, and then the column was washed with 2 bed-volumes of buffer (1.2 l). The eluate and washing buffer were combined and freeze-dried.

The lyophilisate was weighed and, in order to be chromatographed on a column of Biogel P-2, was dissolved in portions in water which had been sterilized by filtration.

Figure 2:
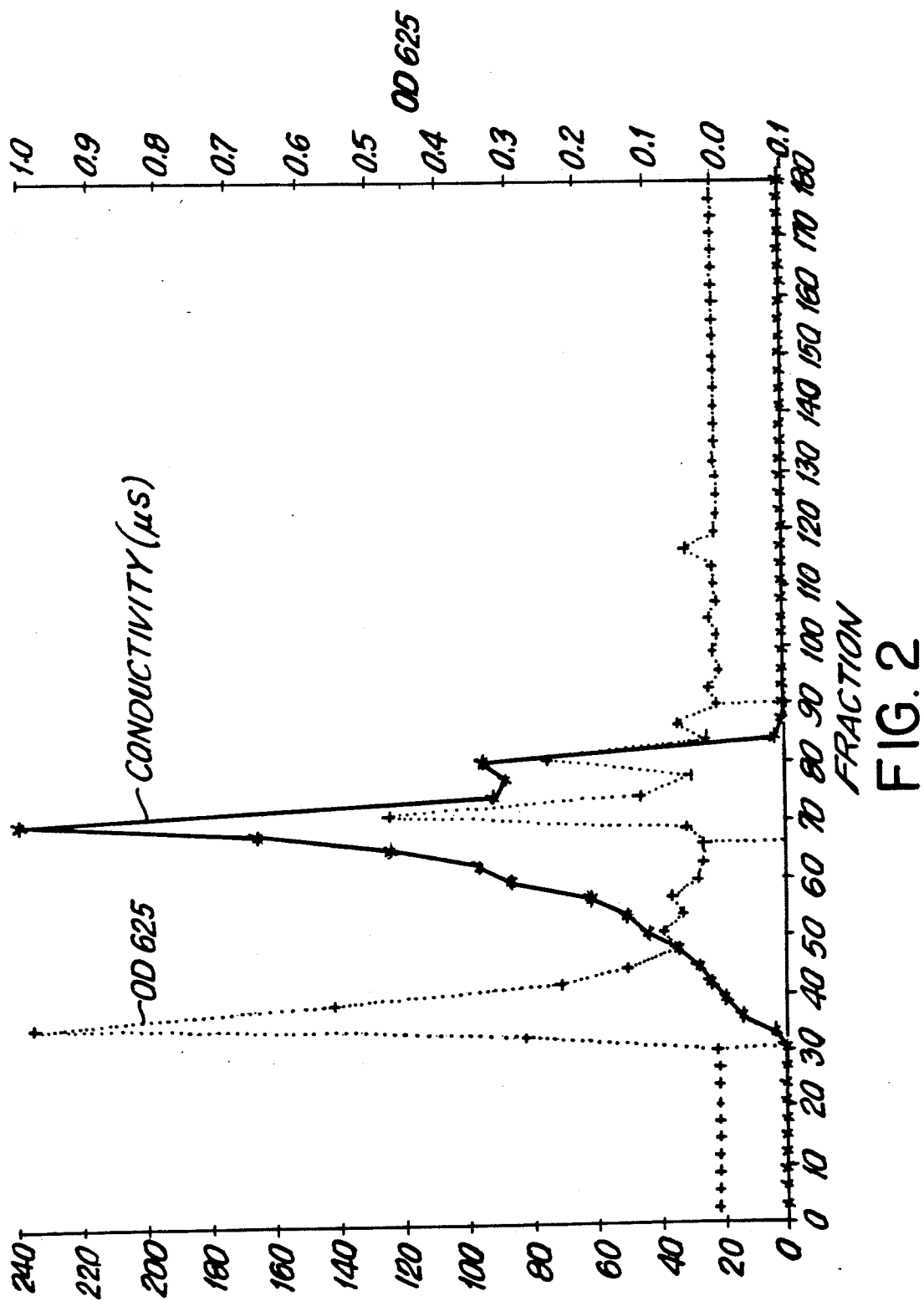
FIG. 2 is an elution diagram of a different degradation product.

Column 2.5×100 cm; bed volume 450 ml; flow ml/h; fraction 4 ml; eluant water; detection by conductivity and the anthrone test (see FIG. 2 for elution profile).

Based on the elution profile of the anthrone test, the carbohydrate-containing fractions were combined and freeze-dried.

Fraction I 179 4 mg
Fraction II 1,223 mg

Fraction I is the cell wall component fraction having the highest immunostimulating action.

D. Purification on QUAE-Sephadex A-25

Fraction I from the P-2 column is taken up in 4.5 ml of distilled H$_2$O, and the solution is applied to a QUAE-Sephadex A-25 column (column volume 100 ml) which had been equilibrated with 0.1 M tris-HCl buffer, pH 6.8, and, after washing with 100 ml of loading buffer, the column was eluted with a linear salt gradient of 0→1 M NaCl in 0.1 M tris-HCl buffer, pH 6.8. In the individual fractions, hexoses were detected by the anthrone test, and uronic acids were detected with carbazole. The combined active fractions were freeze-dried, and salts were removed by gel chromatography on a Biogel P-2 column (2.5×100 cm). Yield: 92.1 mg.

This substance had an immunostimulating action.

Following Example 2, it is also possible as an alternative to use the following steps to obtain immunostimulating cell wall components.

A'. Pronase degradation of the glycoprotein fraction 3.0 g of the glycoprotein fraction from *Halobacterium salinarium* were dissolved in 150 ml of a solution of 0.1 M tris-HCl buffer, pH 7.5, 10 mM CaCl$_2$ and 0.01% by weight of sodium azide, and the solution was centrifuged and incubated with 0.75 g of Pronase E at 39° C. for 15 h. Subsequently a further 0.75 g of Pronase E was added, and the mixture was incubated at 56° C. for 9 h. The mixture was then mixed, in a batch process, with 220 ml of Dowex W50 - X8 (H+form) for 30 min, then filtered with suction, and the solid was washed with 600 ml and 800 ml of H$_2$O. These three different filtrates were combined, neutralized by addition of solid NaHCO$_3$, and freeze-dried.

The material flowing through, together with the two wash phases, were examined for carbohydrate-containing substances using the anthrone test.

Yield:
material flowing through: 2.67 g,
wash phase I: 0.13 g,
wash phase II: 0.02 g.

B'. Purification on Biogel P-10

The lyophilisate from A' was taken up in H$_2$O, and was chromatographed in portions (2 portions) on a Biogel P-10 column (2.5×100 cm; flow: 40 ml/h: with water as eluting agent. The eluate was tested for hexose-containing fractions by the anthrone test, and for uronic acid-containing fractions by the carbazole test (volume of each fraction 4 ml).

Fractions 25-55 and fractions 70-130 were combined and freeze-dried.

Yield:
Fraction I: 0.4 g
Fraction II: 2.4 g

Fraction II: contained the substance with the highest immunostimulating action. cl C'. Purification on Biogel P-2

The freeze-dried fraction II from B' was taken up in distilled H$_2$O, and was chromatographed in portions on a Biogel P-2 column (2.5×100 cm) with water as eluting agent. 4 ml fractions were taken, and detection was based cn color tests for hexoses with anthrone, and for uronic acids with carbazole, as well as the conductivity.

Fractions 30-50 and 51-65, as well as 66-97, were combined and freeze-dried.

Yield:
Fraction I: 320.8 mg
Fraction II: 74.0 mg
Fraction III: 826.7 mg

Fraction I is the glycopeptide fraction having the highest immunostimulating action.

According to a further example, the process according to the invention is carried out as follows:

Example 4

A. Isolation of glycoprotein from *Halobacterium halobium*

2,215 g wet mass of *Halobacterium halobium* was suspended in 3 l of water and disrupted by passing once through a Dyno-Mill (flow rate 0.8 l/h; size of the glass beads about 0.1 mm). To remove lipids, the cells were stirred 2× in 33 l of 2:1 methanol/chloroform mixture for three hours. After the cells had settled overnight, the methanol/chloroform mixture was decanted off. The cells from which lipids had been removed were dried in vacuo at 30° C. for 48 h.

Yield:
630 g

Subsequently, extraction was carried out with 5.0 l of 0.05 M tris buffer solution +0.5% KCl, pH 7.2, which contained 44% phenol, for 3 h. The mixture was centrifuged in a Hettich centrifuge at 2,000 rpm for one hour. The upper aqueous phase was removed and dialyzed against water for 72 h. Insoluble constituents were removed by centrifugation, and the clear supernatant was freeze-dried.

Yield:
4.68 g.

B. Working up of the glycoproteins from *Halobacterium halobium*

4.6 g of the phenol extract were dissolved in 314 ml of 0.1 M tris-HCl buffer, pH 7.5, and 10 mM CaCl$_2$, and 1.575 g of Pronase E were added, and the mixture was incubated at 39° C. for 12 h. Subsequently, a further 1.575 g of Pronase E were added, and the mixture was shaken once more at 56° C. for 12 h.

The solution which had been treated in this way was sterilized by filtration and pumped through a Dowex W50-X8 column (column volume 370 ml) with a flow of 50 ml/h.

The column was washed twice with 500 ml of H$_2$O each time, and the material flowing through and the wash phases were combined and freeze-dried

C. Purification on Biogel P-10

The lyophilisate was taken up in H20 and chromatographed in two portions on a Biogel P-10 column (2.5 x 100 cm) using H20 as eluting agent. 4 ml fractions were taken The anthrone test was used to detect hexoses, and carbazole was used to detect uronic acids.

Fractions 51-77, 78-120 and 120-153 were combined and freeze-dried.

Weight:
Fraction I: 492 mg
Fraction II: 786 mg
Fraction III: 4,102 mg

The three fractions were tested for an immunostimulating action. Fraction I showed the greatest action.

D. Purification on QUAE-Sephadex A-25

360 ml of QUAE-Sephadex A-25 were equilibrated with 0.15 M ammonium formate buffer, pH 4.0. Fraction I from the chromatography on Biogel P-10 was taken up in the same buffer and applied to the column, which was washed with one column volume of loading buffer (flow 50 ml/h). Subsequently, a linear salt gradient of 0.15→2 M ammonium formate, pH 4.0, was applied. The main component (anthrone test, uronic acid test) eluted at an ammonium formate concentration of about 0.77 M. The appropriate fractions were combined and freeze-dried.

E. Removal of salts on Biogel P-2

The freeze-dried main component from the anion exchange chromatography was taken up in 50 ml of $H_2O$ and submitted to gel chromatography on a Biogel P-2 column (5 × 100 cm) eluting with a flow of 100 ml/h $H_2O$. Each of the 8.5 ml fractions was examined for hexoses by the anthrone test and for the salt content by conductivity measurements. The carbohydrate-containing fractions (fractions 60–80) were combined and freeze-dried.

Yield:

93 mg

This glycopeptide was tested for an immunostimulating action.

The cell wall components prepared according to the invention have a broad defense-enhancing action.

Substances which stimulate the body's defenses (immune system, phagocytosis) during an infection are of great interest for both human and veterinary medicine, because, despite satisfactory possibilities for chemotherapy, many infections persist where there is no assistance from the body's defense mechanisms. This may result in renewed appearance of symptoms (recurrence) after the initial disease has been overcome, and thus in chronic recurrent illnesses. Among the diseases caused by bacteria, particular problems are posed by infections with facultative intracellular bacteria.

An experimental model for a disease of this type is infection of the mouse with Salmonella typhimurium.

Inoculation of mice with these human pathogenic bacteria is followed by an illness which has a subacute to chronic course, depending on the infectious dose, in which the animals do not start to die until 4 to 7 days have elapsed. During this period it is possible for substances to have an effect on the immune system. High germ counts are found in the blood and in the liver and spleen of infected animals during the first two weeks. The germ counts then gradually decrease, but are still detectable 8–12 weeks after the inoculation. In most other infections of experimental animals, the animals start to die very rapidly, within 1 to 2 days. Hence there is no longer any possibility of stimulating the defenses during the infection.

It is also known that N-acetyl-muramyl-L-alanyl-D-isoglutamine, the smallest active component from the cell wall of mycobacteria, stimulates the unspecific defense against infections (Robert Koch Stiftung e.V., Beiträge und Mitteilungen Vol. 5/1983, pages 31–38).

It has now been found, surprisingly, that the cell wall components prepared according to the invention are also able to increase the unspecific defenses against infections. This finding is based on the following experiments:

1. Reduction in the germ count

The cell wall components were administered once, either intraperitoneally or subcutaneously, in various doses to mice before infection, specifically one day before subcutaneous infection with $2 \times 10^5$ colony-forming units (CFU) of Salmonella typhimurium. In untreated animals, this infectious dose results in a high germ count in the blood and in the organs, especially liver and spleen, on day 3. The animals were housed in Makrolon cages under constant conditions (22° ± 2° C.; 55–65% relative atmospheric humidity) and received Ssniff diet for experimental animals.

In several experiments, treatment of the animals with cell wall components in dosages of 0.1, 1, 10 or 100 mg/kg active compound was followed by a significant reduction in the germ counts in the blood of infected mice compared with animals which had not been treated.

2. Lethality

After a single subcutaneous dose of 0.1, 1.0 or 10 and 25 mg/kg before lethal infection with Salmonella typhimurium, the substances of the invention significantly increased the survival rate, and this is still detectable on day 42 after infection.

Compared with untreated animals, the treatment of mice which had been infected with 10 times the $LD_{50}$ of the bacteria resulted in a significant increase in the survival rate and the prolongation of the survival time (see table).

TABLE

Effect of components from archaebacteria (Halobacterium salinarium) in a model infection

| | CWC 56/2 1 | | CWC 71 | |
|---|---|---|---|---|
| Dose[a] mg/kg | Mean survival time (days) | Survival rate (day 42) | Mean survival time (days) | Survival rate (day 42) |
| 0.1 | 38 | 12/24[b] | 23 | 7/24 |
| 1.0 | >42 | 15/24[c] | 28 | 11/24[b] |
| 10.0 | >42 | 17/24[c] | >42 | 14/24[c] |
| Control | 7.5 | 4/24 | 7.5 | 4/24 |

[a] Single subcutaneous dose 24 hours before lethal infection with Salmonella typhimurium
[b] p <0.05, Fisher test.
[c] p <0.005, Fisher test.

These effects were found on parenteral administration of the substances. On parenteral administration, they result in a distinct reduction in the bacteria counts in the blood and in the liver, specifically after intraperitoneal infection with so-called intracellular bacteria, ther is to say bacteria which continue to proliferate after uptake into the macophages—the most important cells of the unspecific defenses—until these cells in the immune system are activated and thus made able to kill the bacteria intracellularly.

3. Granulocytic activity

Figure 3:
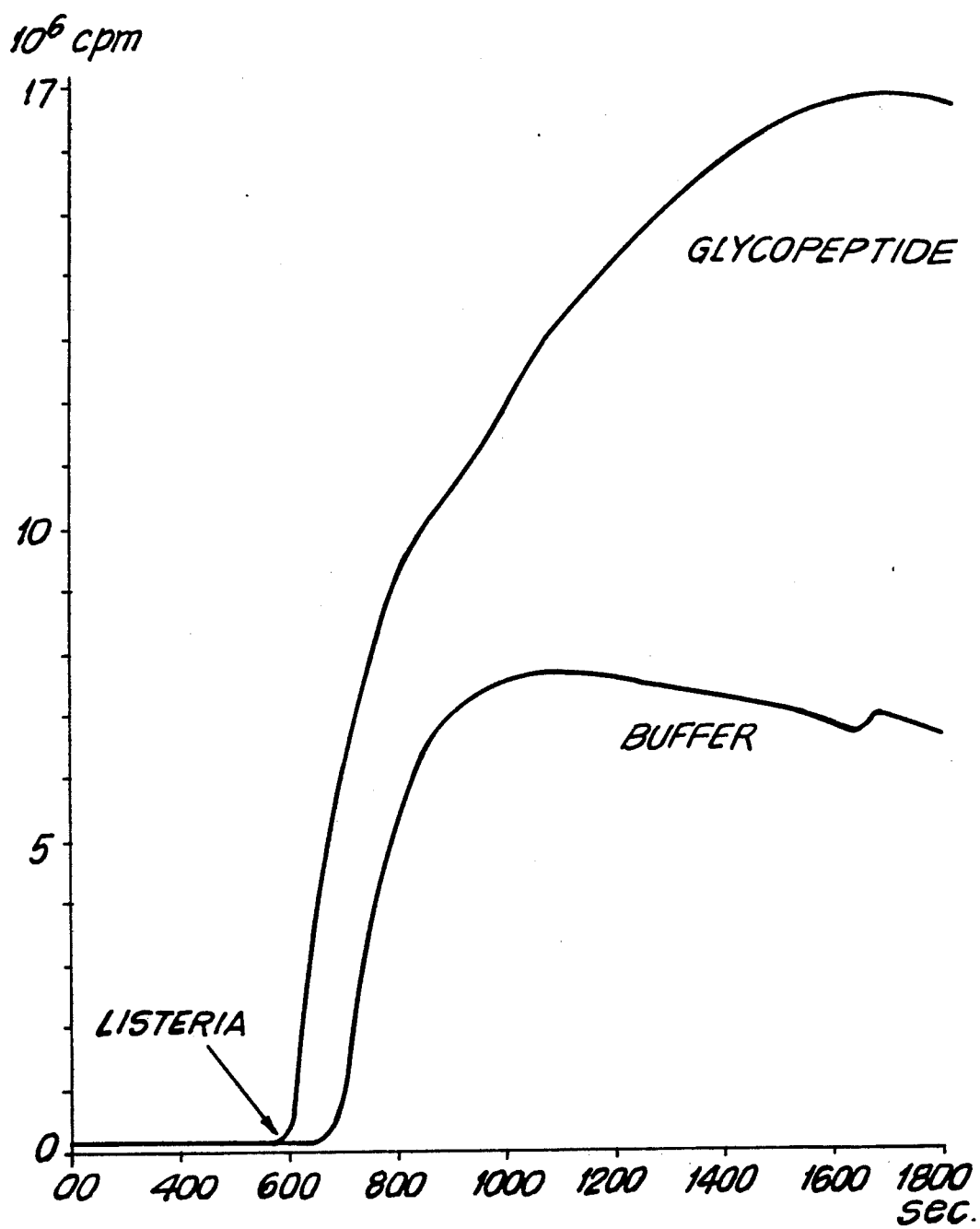
FIG. 3 is a plot of Listeria-induced chemiluminescence on granulocyte activity.

The phagocytes are an important constituent of the unspecific defenses against infection. They are able to intervene very early in the infectious event and to defend against invading pathogens. An important part is played in this by the toxic and reactive oxygen species ($O_2^-$, $H_2O_2$, $OH$, $^1O_2$) which are produced in the oxidative metabolism of the phagocytes and have antimicrobial properties Using the method of luminol-dependent chemiluminescence measurement, it is possible to examine changes in activity of the oxidative metabolism of the phagocytes under various conditions, including under the influence of substances. Corresponding studies have been carried out on neutrophilic granulocytes from peripheral human blood: the direct influence of the glycoprotein from archaebacteria on human granulocytes, and the effect of the substance on the granulocyte activity induced by Listeria, were investigated. The glycoprotein alone had no effect on granulocyte activity. However, the Listeria induced chemiluminescence of granulocytes was distinctly enhanced in the presence of the glycoprotein, 100 μg/$10^6$ cells/ml (FIG. 1). Even at a concentration of 0.01 μg/$10^6$ cells/ml, there was an observable effect, although slight, on granulocyte activity (FIG. 3).

The pharmaceutical products of the present invention are preferably tablets or gelatin capsules which contain the active compounds together with diluents, for example lactose, dextrose, sucrose, mannitol, sorbitol or cellulose, and/or lubricants, for example diatomaceous earth, talc, stearic acid or salts thereof, such as magnesium or calcium stearate, and/or polyethylene glycol. Tablets also contain binders, for example magnesium aluminum silicate, starches such as corn wheat, rice or arrowroot starch, gelatin, tragacanth, methylcellulose, sodium carboxymethylcellulose and/or polyvinylpyrrolidone, and, if desired, disintegrants, for example starches, agar, alginic acid or a salt thereof, such as sodium alginate, and/or effervescent mixtures, or adsorbents, colorants, flavorings and sweeteners.

Injectable products are preferably isotonic aqueous solutions or suspensions. Suppositories, ointments or creams are primarily fatty emulsions or suspensions. The pharmaceutical products can be sterilized and/or contain auxiliaries, for example preservatives, stabilizers, wetting agents and/or emulsifiers, solubilizers, salts to regulate the osmotic pressure and/or buffers. The present pharmaceutical products, which, if desired, may contain further pharmacologically valuable substances, are prepared in a manner known per se, for example by conventional mixing, granulating or coating processes, and contain from about 0.1% to about 75%, in particular from about 1% to 50%, of the said active compounds.

It will be appreciated that the instant specification and claims are set forth by way of illustration and not limitation, and that various modifications and changes may be made without departing from the spirit and scope of the present invention.

What is claimed is:

1. A pharmaceutical composition for unspecific defense against infection comprising a pharmaceutically acceptable carrier and an amount effective to unspecifically defend against infection of native cell wall glycoproteins of Halobacteria, or the enzymatic cleavage products thereof.

2. The pharmaceutical composition according to claim 1, where the archaebacteria are selected from the group *Halobacterium salinarium* (DSM 668) and *Halobacterium halobium* (DSM 671).

3. The pharmaceutical composition according to claim 1, wherein the cleavage products are obtained by enzymatic degradation.

4. The pharmaceutical composition according to claim 3, wherein the degradation is carried out with at least one of trypsin, subtilisin, pronase, chymotrypsin, pepsin, proteinase K, papain, carboxypeptidase A, B, P or Y, elastase, pepsin and thermolysin.

5. The pharmaceutical composition according to claim 3, wherein the degradation is carried out with trypsin, and the glycopeptide fraction obtained thereby is further degraded with subtilisin.

6. The pharmaceutical composition according to claim 3, wherein the degradation is carried out with pronase.

7. A method of unspecifically defending a patient against infection, which comprises administering to such patient an amount effective therefor of native cell wall glycoproteins of Halobacteria, or the enzymatic cleavage products thereof.

* * * * *